(12) United States Patent
Vinayagamoorthy

(10) Patent No.: US 7,727,745 B2
(45) Date of Patent: Jun. 1, 2010

(54) SYNTHESIS OF SINGLE-STRANDED DNA

(75) Inventor: Thuraiayah Vinayagamoorthy, Saskatoon (CA)

(73) Assignee: Bio-ID Diagnostic Inc., Edmonton, AB (CA)

( * ) Notice: Subject to any disclaimer, the term of this patent is extended or adjusted under 35 U.S.C. 154(b) by 426 days.

(21) Appl. No.: 11/464,273

(22) Filed: Aug. 14, 2006

(65) Prior Publication Data

US 2008/0118915 A1   May 22, 2008

(51) Int. Cl.
*C12P 19/34* (2006.01)
*C07H 21/02* (2006.01)

(52) U.S. Cl. .................... 435/91.2; 536/23.1
(58) Field of Classification Search .............. None
See application file for complete search history.

(56) References Cited

U.S. PATENT DOCUMENTS

| 5,674,734 | A * | 10/1997 | Leder et al. ............... 435/252.3 |
| 5,811,240 | A * | 9/1998 | Ferreira et al. ............... 435/6 |
| 6,197,510 | B1 | 3/2001 | Vinayagamoorthy |
| 6,355,484 | B1 | 3/2002 | Patten et al. |
| 2003/0152984 | A1* | 8/2003 | Aygun et al. ............... 435/6 |
| 2004/0101893 | A1* | 5/2004 | Kutyavin et al. ............ 435/6 |
| 2004/0163140 | A1* | 8/2004 | Morgan et al. ............ 800/17 |
| 2005/0123950 | A1* | 6/2005 | Mukai et al. ............... 435/6 |
| 2006/0078924 | A1* | 4/2006 | Finn et al. ............... 435/6 |
| 2007/0020639 | A1* | 1/2007 | Shapero ............... 435/6 |
| 2008/0118915 | A1 | 5/2008 | Vinayagamoorthy |

FOREIGN PATENT DOCUMENTS

| WO | WO 01/64864 A2 | 9/2001 |
| WO | WO 2004/083427 A2 | 9/2004 |

OTHER PUBLICATIONS

Walker et al. Strand displacement amplification-an isothermal, in vitro DNA amplification technique. Nucleic Acids Research 20(7):1691-1696 (1992).*
Microcon® Centrifugal Filter Devices Data Sheet (hereinafter "Microcon") [online] Jul. 1998 [retrieved on Nov. 11, 2008] retrieved from: http://www.millipore.com/publications.nsf/a73664f9f981af8c852569b9005b4eee/962a1b2daa713f34852568f90063d733/$FILE/ATTI7MZ1/P185.pdf (6 pages).*

(Continued)

*Primary Examiner*—Young J Kim
*Assistant Examiner*—Samuel C Woolwine

(57) ABSTRACT

A method of producing single-stranded DNA. In one form, the method involves providing a uracil-containing oligonucleotide template molecule having a sequence that is complementary to a part of a target single-stranded DNA molecule of length greater than the template molecule; providing one or more parts of the target molecule including a base sequence complementary to a part of the template molecule; annealing the part(s) of the target molecule to the template molecule and forming the complete target molecule by ligating together at least two adjacent parts of the target molecule while annealed to the template molecule, and/or extending at least one part of the target molecule to form a sequence complementary to a remainder of the template molecule by nucleotide polymerization, and then separating the template molecule from the target molecule. In another form, an intermediate molecule is annealed to the template and then enzymatically cut, and one part is then extended by DNA polymerization using monomers of increased molecular weight or ionic charge compared to the monomers used to form the intermediate molecule.

7 Claims, 4 Drawing Sheets

OTHER PUBLICATIONS

Craig et al. Labelling oligonucleotides to high specific activity (I). Nucleic Acids Research 17(12):4605-4610 (1989).*

Ball, Jonathan K. and Desselberger, Ulrich, 1992, *The use of uracil-N-glycosylase in the preparation of PCR products for direct sequencing*, Nucleic Acids Research, vol. 20, No. 12, pp. 3255.

Sambrook and Russel, 2001, *Molecular Cloning—A Laboratory Manual*, Cold Spring Harbor Laboratory Press, 3rd edition.

Kelly, W.S., Chalmers, K. and Murray, N.E., *Isolation and characterization of a lambdapolA transducing phage*; Proc. Natl. Acad. Sci., USA, vol. 74, No. 12, pp. 5632-5636, Dec. 1, 1977.

* cited by examiner

SYNTHESIS OF SINGLE-STRANDED DNA

BACKGROUND OF THE INVENTION

1. Field of the Invention

This invention relates to methods of synthesis of single-stranded DNA or like polynucleotides of desired nucleotide sequence. More particularly, the invention relates to methods of synthesis of long stretches of single-stranded DNA of increased length and/or molecular weight.

2. Background Art

Short lengths of single-stranded DNA are used in a number of techniques employed in molecular biology, for example as primers employed in DNA amplification using the polymerase or ligase chain reaction (PCR or LCR), as primers used for DNA sequencing, or as labeled probes used for sequence identification in samples of DNA. Such short lengths of single-stranded DNA are normally produced by attaching a base nucleotide to a solid support and then linking one nucleotide at a time to the growing chain to create a nucleotide polymer of predetermined sequence. This is generally carried out within a commercial nucleic acid synthesizer. However, the greater the length of the DNA strand produced in this way, the lower is the purity of the resulting product (i.e. errors in the desired sequence are more likely as the sequence length increases). Acceptably pure sequences up to 100 bases in length may be synthesized with some difficulty, but sequences of more than 80 bases are not normally produced in this way. Indeed, sequences of only 20-35 base pairs are most commonly produced using such techniques. For short primers required for PCR or DNA sequencing, this limitation on sequence length is not usually a problem. However, other techniques may require sequences of 100 bases or more, e.g. those designed to introduce restriction sites into DNA molecules, those used in a multi-loci gene sequencing technique described in U.S. Pat. No. 6,197,510 issued to T. Vinayagamoorthy on Mar. 6, 2001, or those involving the synthesis of genes or for use in making microcircuits by means of nanotechnologies. Additionally, there are applications where DNA molecules of increased molecular weight or ionic charge for a given sequence length would be of benefit, e.g. in the multi-loci gene sequencing technique mentioned above.

There is therefore a need for a method of reliably synthesizing nucleic acid molecules of greater length and/or increased molecular weight or ionic charge than those produced by conventional techniques, while maintaining acceptable purity and the ability to determine a desired nucleotide sequence.

SUMMARY OF THE INVENTION

In the present invention, use is made of a template molecule to anneal to one or more parts of a larger target molecule while the target molecule is constructed. The template molecule may then be removed by digestion. Both the template molecule and the one or more parts of the target molecule are short enough to be synthesized by conventional techniques (e.g. they are of 100 bases or less, preferably 80 bases or less and, more preferably, 60 bases or less). Nevertheless, a target molecule of larger size can be assembled by ligation or constructed polymerization from the smaller part or parts. By incorporating uracil into the template molecule, a digestion enzyme specific to uracil, e.g. Uracil-N-glycosylase (UNG), may then be used to remove the template, thus freeing the target DNA molecule (which, like all DNA, contains no uracil).

Thus, an exemplary embodiment of the present invention provides a method of producing single-stranded DNA. The method comprises providing an oligonucleotide template molecule having a sequence that is complementary to a part of a target single-stranded DNA molecule of length greater than the template molecule, the template oligonucleotide incorporating one or more uracil bases; providing at least one part of the target molecule including a base sequence complementary to a part of the template molecule; annealing the at least one part of the target molecule to the template molecule and forming the complete target molecule by a method selected from the group consisting of ligating at least two adjacent parts of the target molecule while annealed to the template molecule, extending at least one part of the target molecule to form a sequence complementary to a remainder of the template molecule by nucleotide polymerization, and a combination of both the ligating and extending methods; and separating the template molecule from the target molecule.

The separating of the template molecule from said target molecule is preferably carried out by digesting the template molecule with a digestion enzyme specific to molecules containing uracil bases, e.g. uracil-N-glucocylase (the enzyme chemically cuts the template into fragments). However, other techniques may be employed, e.g. by employing heat and/or alkali to pH 12.0, but are often less desirable. The enzymatic method does not have to be followed by filtration, although this is normally done for greater purity and for downstream purposes. Techniques involving separation by heat or alkali have to be followed by filtration under conditions favoring separation to prevent re-annealing of the template and the target.

Preferably, the target molecule part(s) and the template each has a length smaller than 100 bases, more preferably smaller than 80 bases, and the target molecule has a length of 100 bases or more.

If necessary, following the separation of the target molecule from said template, the target molecule is isolated from other reaction products and starting materials by a suitable method, e.g. by membrane filtration.

Another exemplary embodiment of the invention provides a method of producing a single-stranded polynucleotide molecule, which comprises: providing a template polynucleotide molecule having a sequence of bases complementary to a target polynucleotide molecule, the template sequence including at least one uracil base; annealing to the template molecule an intermediate polynucleotide molecule having a sequence complementary to the template molecule; cutting (nicking) the intermediate polynucleotide molecule into two fragments while annealed to the template molecule and extending one of the fragments to replace the other by nucleotide polymerization employing nucleotide monomers of increased molecular weight or ionic charge compared to nucleotide monomer residues forming the intermediate molecule, thereby forming the target polynucleotide molecule having sequence complementary to the template; and separating the template from the target polynucleotide molecule, thereby forming a single-stranded target polynucleotide molecule, which is preferably isolated from remaining reaction components.

This exemplary embodiment can be used to prepare single-stranded DNA sequences that may be of a length that can be produced economically by conventional techniques, but includes a fragment that is of increased molecular weight or ionic charge compared to "natural" DNA, i.e. DNA that incorporates dNTPs found in natural DNA. The resulting single-stranded DNA may be used, for example, as probes used for PCR or DNA sequencing that creates fragments of increased molecular weight or ionic charge compared to fragments of similar numbers of base pairs, thereby enabling improved separation from such fragments using gel electrophoresis or the like.

According to yet another exemplary embodiment of the invention, there is provided a method of producing a single-stranded polynucleotide molecule, which comprises: providing a template polynucleotide molecule comprising at least one uracil base and having a sequence that is complementary to at least a part of a target polynucleotide molecule; providing an additional polynucleotide molecule having a sequence corresponding to at least a part of the target molecule; allowing the template molecule and the additional molecule to anneal together; modifying the additional molecule while annealed to the template to form the target molecule; separating the target molecule from the template by providing an enzyme that digests polynucleotides containing uracil bases, thereby freeing the target molecule as a single-stranded polynucleotide; and isolating the single-stranded target molecule from remaining reaction products and starting materials.

DETAILED DESCRIPTION OF THE PREFERRED EMBODIMENTS

As is well known, DNA is a polymer comprising a chemically-linked chain of nucleotide monomers, each of which consists of a sugar (deoxyribose), a phosphate and one of four kinds of nucleobases ("bases"), namely adenine (A), thymine (T), cytosine (C), and guanine (G). A DNA molecule is able to anneal (i.e. reversibly join to) a second strand of DNA having a complementary sequence of bases, that is to say, a sequence where there is a T on one strand aligned with an A on the other, and a G on one strand aligned with a C on the other. However, the base uracil (U) is also complementary to A, so a molecule having one or more of its T bases replaced by U will anneal to a complementary strand having an aligned A for every U. The base uracil does not normally occur in DNA (it is a component of RNA), so synthesized DNA target molecules normally do not contain U.

In one form of the present invention, it is possible to synthesize a single-stranded DNA molecule of greater length (e.g. 100 nucleotides or more) than those normally produced by conventional techniques and that has a predetermined base sequence. Such a molecule is referred to herein as a target DNA molecule (i.e. a molecule that is desired to be produced). In this form of the invention, a template molecule is first constructed. This is a polynucleotide of a length that can be synthesized by conventional techniques and having a sequence that is complementary to a part of the intended sequence of the target DNA molecule, but including at least one U instead of a T that would normally be present. The reason for this substitution will be apparent from the description below.

Figure 1:
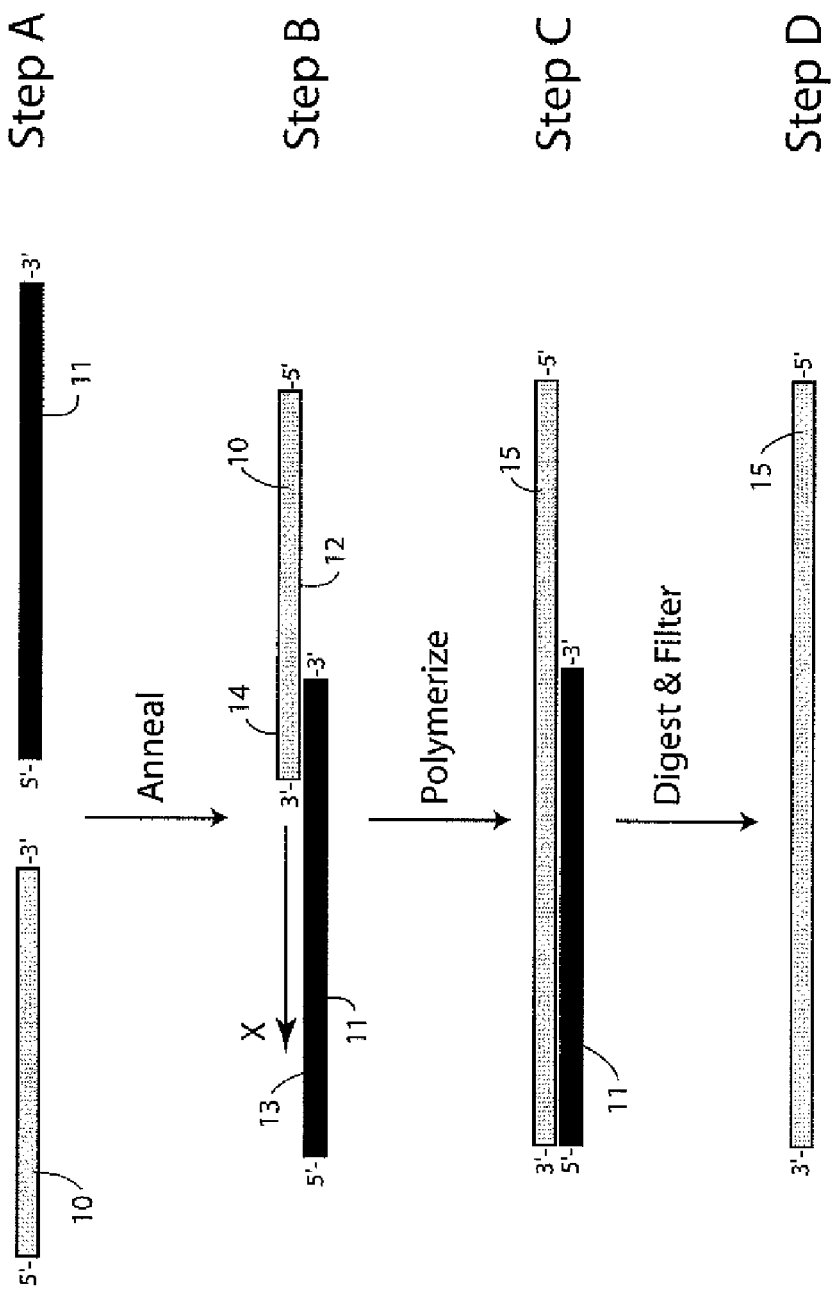
FIG. 1 is a diagram illustrating, in simple form, one possible method according to the present invention.
Figure 2:
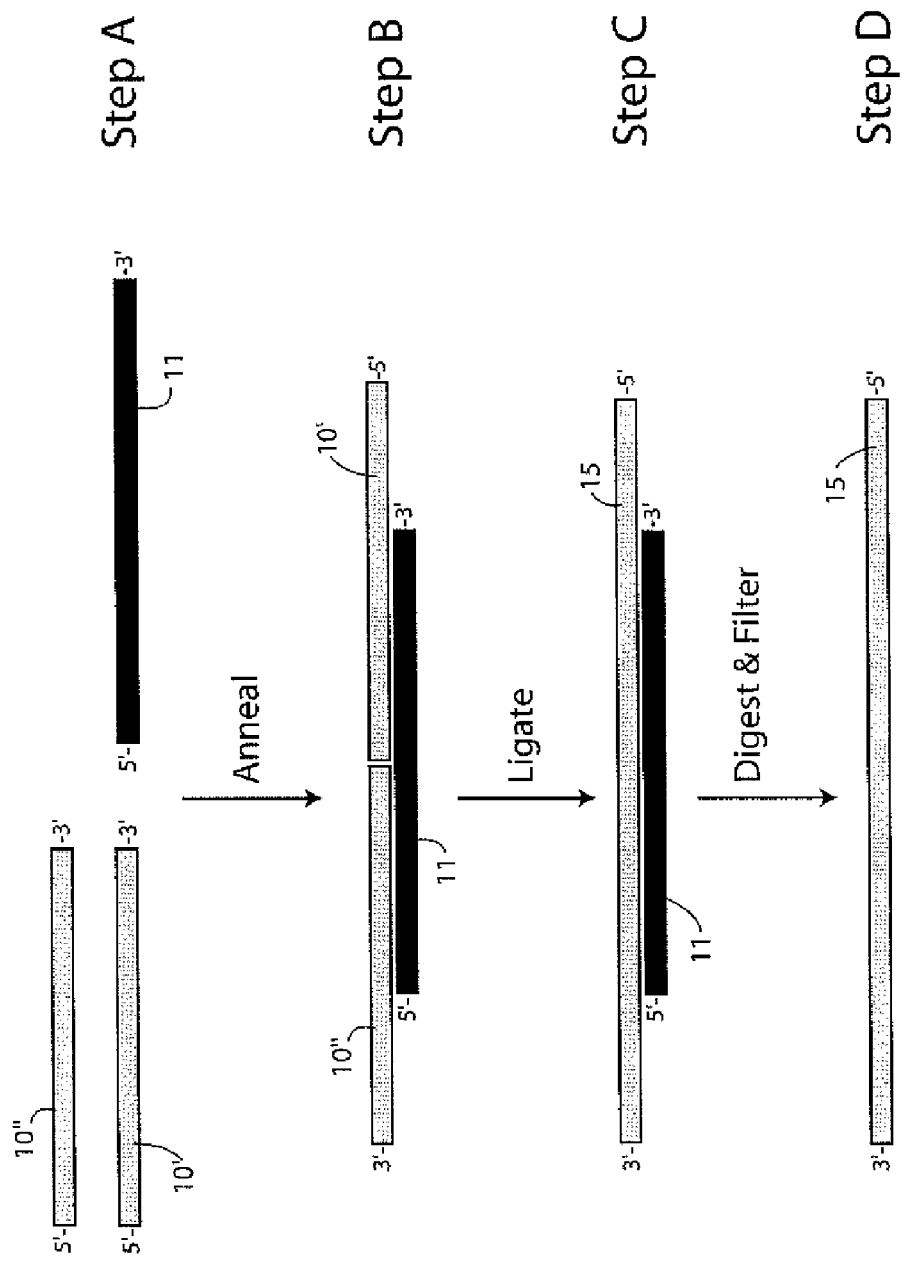
FIG. 2 is a diagram illustrating, in simple form, a second possible method according to the present invention.

At least one short part of the target molecule is then also synthesized using a conventional technique, and the template molecule and target part(s) are allowed to anneal. The completion of the construction of the target molecule then follows by one of at least two procedures. The two procedures are illustrated in simple form in FIGS. 1 and 2 of the accompanying drawings. FIG. 1 illustrates a polymerization technique and FIG. 2 illustrates a ligation technique.

In FIG. 1, Step A represents the provision of both one part 10 of a target molecule and a template molecule 11. The method of synthesizing the target part and template may be carried out conventionally, for example, as disclosed in *Molecular Cloning*: A Laboratory Manual, by Sambrook and Russel, 3rd Edition, Cold Spring Harbor Laboratory Press, 2001 (the disclosure of which is incorporated herein by reference). In the illustration of FIG. 1, the target part 10 has 50 bases, whereas the template molecule has 75 bases. Since the full sequence of the target molecule is known in advance, it is a simple matter to design the sequence of the template so that the target part and the template will anneal in a desired manner. The template molecule 11 is formed using uracil triphosphate (UTP) as a monomer instead of thymine triphosphate (TTP) during the conventional synthesis so that the template will have Us instead of Ts, the Us being positioned in the sequence to align with every A of the complementary part of the target sequence. It is normal to construct the template without any Ts at all, but this is not essential. There should, however, be at least one U in the template sequence, and preferably several, e.g. one every two or three nucleotides. Indeed, the template may consist entirely of Us, provided that the target sequence is intended to include a complementary stretch of all As.

Step B shows the annealing together of these two molecules. It will be seen that the sequence of the template 11 is made such that it overlaps (i.e. is complementary to) one end of the target part 10, so that both the target part 10 and the template 11 have overhanging non-annealed sections 12 and 13, respectively, and an annealed section 14 of 25 bases each. The resulting annealed construct is then used as a base for polymerization of the remainder of the target molecule 15, extending from the 3' end of the target part 10 in the direction of the arrow X. This can be done by using a DNA polymerization technique, such as that used for PCR employing the enzyme Taq polymerase and a mixture of nucleotide monomers under suitable conditions. The new sequence is complementary to the previously unaligned part 13 of the template molecule 11. For further details of the DNA polymerization technique, reference may again be made to *Molecular Cloning*: A Laboratory Manual, by Sambrook and Russel, 3rd Edition, Cold Spring Harbor Laboratory Press, 2001 (the disclosure of which is incorporated herein by reference).

As shown in Step C, the additional bases added in this way produce a target molecule 15 of 100 bases, 50 of which correspond to the sequence of the original target molecule part 10 and the remaining 50 of which are complementary to the overhanging sequence 13 of the template molecule 11.

The template molecule 11 is preferably constructed using a dideoxynucleotide at the 3' end of the molecule so that the DNA polymerization reaction does not extend the template itself. The template 11 therefore remains shorter than the target molecule 15.

After completion of the DNA polymerization reaction, the target molecule 15 remains annealed to the template 11 in the form of double-stranded DNA. However, the template molecule may be digested and disintegrated, for example by the addition of an enzyme (e.g. uracil-N-glycocylase) that cuts the molecule at the U bases. Uracil-N-glycocylase is a commercial enzyme that may be obtained, for example, from Applied Biosystems, USA under trade name AmpErase®. As instructed by the manufacturer, the reaction is carried out at 50° C. for 5 minutes and then heated at 95° C. for 15 to 30 minutes to denature the enzyme. Basically, the template is cut into small fragments of the original molecule, the fragments being individual bases or short sequences of two or three bases depending on the number of Us in the template sequence. Since the target molecule 15 does not have any U bases, it remains undigested and exists as single-stranded DNA.

As shown in Step D, the target molecule 15 (which is the molecule with the highest molecular weight in the reaction mixture) may be removed from other components of the digestion product (e.g. digested fragments of the template and unextended target parts) by any suitable method, such as membrane filtration using a 100 base cut-off (e.g. a filter from PSI clone, Princeton Separation, New Jersey, USA), or a gel matrix such as Sephadex® used for size exclusion. This allows any remaining target parts and small fragments to be separated out, thus providing a purified single-stranded DNA target molecule 15 of 100 bases in length. Although, prior to filtration, some of the template fragments may re-anneal to complementary parts of the target molecule, these fragments do not adhere strongly (because of the small number of bases in such fragments) and they are normally freed from the target molecule during the separation step.

The procedure may be carried out commencing with concentrations or quantities of the starting materials in micromoles or micro-grams, but increased concentrations or quantities may be employed as required. If it is desired to amplify the resulting target DNA, this may be done by employing conventional polymerase chain reaction, thereby increasing the quantity of the product significantly.

The illustrated method may then be repeated using the target molecule of one or two of such procedures as target molecule parts for a further procedure using a suitable new template, thereby creating a target molecule of significantly increased length. Additional repetitions of the procedure will cause the length of the target molecules to increase significantly. Hence, very long target molecules may be formed without incurring unacceptable impurity of the product. This is illustrated in the Table below:

TABLE

| Template length (mer*) | Target annealing length (mer) | Initial target length (mer) | Final target length (mer) |
|---|---|---|---|
| 50 | 20 | 50 | 80 |
| 50 | 20 | 80 | 110 |
| 50 | 20 | 110 | 140 |
| 50 | 20 | 140 | 170 |
| 50 | 20 | 170 | 200 |
| 50 | 20 | 200 | 230 |
| 50 | 20 | 230 | 260 |
| 50 | 20 | 260 | 290 |
| 50 | 20 | 290 | 320 |
| 50 | 20 | 320 | 350 |
| 50 | 20 | 350 | 380 |
| 50 | 20 | 380 | 410 |
| 50 | 20 | 410 | 440 |
| 50 | 20 | 440 | 470 |
| 50 | 20 | 470 | 500 |
| 50 | 20 | 500 | 530 |
| 50 | 20 | 530 | 560 |
| 50 | 20 | 560 | 590 |

*The term "mer" means a molecule that forms a building block for the polymer structure and is equivalent to the number of bases.

In theory, there is no limit to the size of the target molecule that may be produced in this way, but sequences up to 1000 bases (1000 mer) are probably most suitable for current practical applications. However, for applications such as the construction of whole genes or expression short tags (ESTs) (also known as expressed sequence tags), lengths of one or two kilobases may be desirable.

In the alternative procedure of FIG. 2, Step A shows the formation of two target molecule parts 10' and 10" (each of 50 bases), and a template 11 of 75 bases (again comprising at least one U). It should be noted that the two target molecule parts 10' and 10" may, in particular cases, be identical. The sequence of the template 11 is made such that it will anneal with both of the two target parts 10' and 10" such that the target molecule parts become aligned adjacent to each other as shown in Step 3. Ideally, the two target molecule parts are aligned without a gap, but a gap of one base may be tolerated.

The two target molecule parts are then joined by ligation to form the target molecule 15 as shown in Step C. The subsequent steps digestion and purification steps (Step D) may then be the same as in the embodiment of FIG. 1.

The ligation step is carried out in the presence of a suitable ligase enzyme, preferably T4 DNA ligase (which may be obtained, for example, from New England Biolabs Inc. of Ipswich, Mass., USA). This enzyme (which originates from T4 bacteriophage) catalyzes the formation of a phosphodiester bond between juxtaposed 5' phosphate and 3' hydroxyl termini in DNA. The process is essentially the same as that carried out during the ligase chain reaction (LCR) and is usually carried out in the presence of a buffer that contains adenosine triphosphate (ATP), e.g. at a concentration of 0.25 to 1 mM. Most restriction enzyme buffers will be suitable for this purpose. The mixture is incubated at a suitable temperature, optimally 16° C., for a suitable time, such as 30 minutes to two hours. Essentially, this reaction forms one piece of DNA from two.

In both the ligation procedure and the polymerization procedure, it is possible to employ more than one template and appropriate parts of the target molecule that anneal with such templates simultaneously. However, this may reduce the purity of the resulting target molecule product.

Thus, the invention allows a relatively short part or parts of a target molecule to be synthesized by conventional techniques, and then enables the full target molecule to be produced in a way that avoids the formation of incorrect or impure sequences. Relatively long sequences can therefore be produced on a reliable basis.

Figure 3:
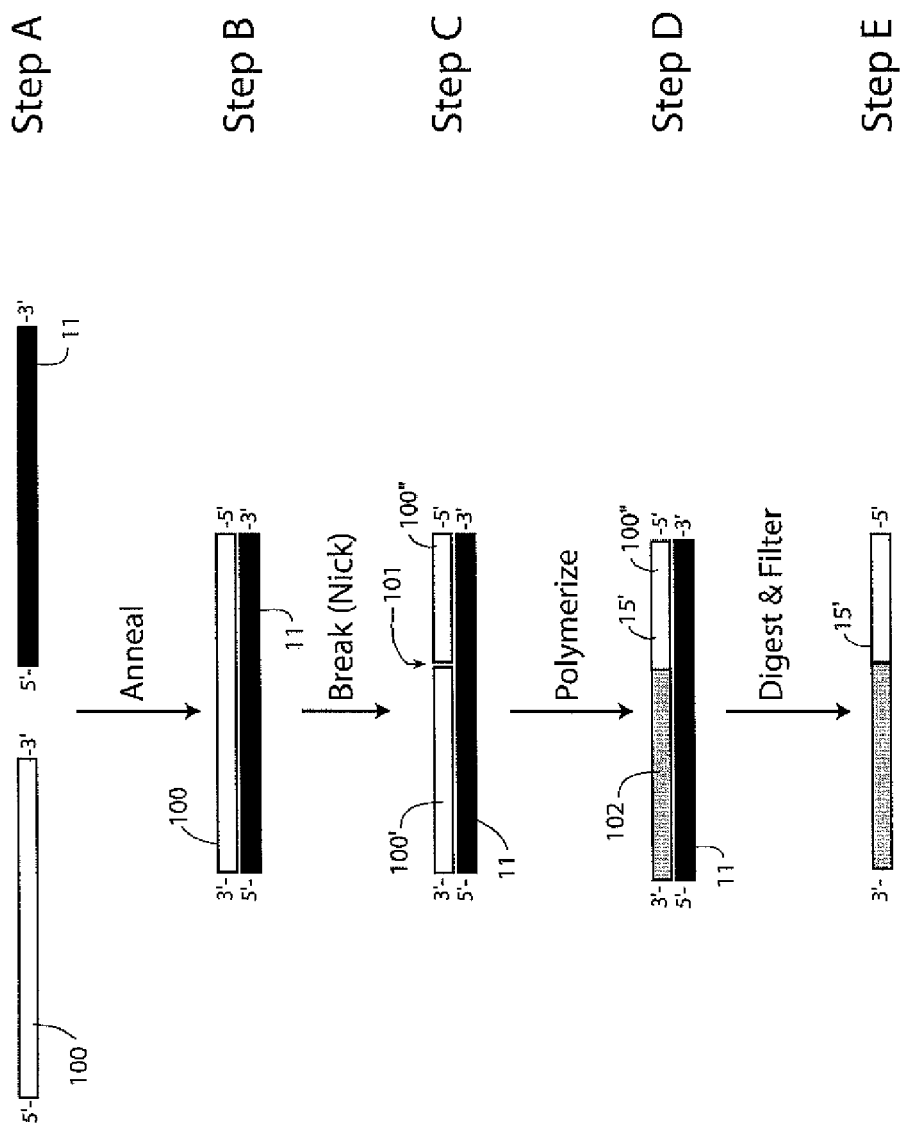
FIG. 3 is a diagram illustrating, in simple form, an alternative embodiment of the invention.

Another form of the invention involves a variation of the polymerization process described above. This is illustrated in FIG. 3. In this form of the invention, the intention is not to produce a single strand of DNA that is necessarily longer than the template molecule, but one that has a different (preferably higher) molecular weight or ionic charge than would normally be the case for a polynucleotide molecule of the same number of bases. As shown in Step A, an intermediate molecule 100 is provided as well as a template molecule 11. The intermediate molecule and template are of the same length and have complementary sequences. However, the template 11 is formed with a U in place of at least one T, as in the previous forms of the invention. The intermediate molecule 100 is a strand of conventional DNA produced as single-stranded molecule by conventional DNA synthesis and is normally of less than 100 bases in length, and the template molecule 111 is also produced by a conventional method. The intermediate molecule 100 and template 11 are allowed to anneal to form a double-stranded molecule, as shown in Step B, which is then provided with a break 101 (or "nick") in the phosphodiester backbone of the molecule by reaction with a deoxyribonuclease enzyme (e.g. deoxyribonuclease 1, often designated Dnase 1) to produce two fragments 100' and 100", as shown in Step C. One of the fragments 100' is removed and, as shown in Step D during the polymerization, the remaining fragment 100" is extended by DNA polymerization using deoxynucleotides (dNTPs) of increased molecular weight or ionic charge compared to those forming the intermediate molecule 100 (which are normally "conventional" dNTPs found in nature). This produces a target polynucleotide 15' that is a hybrid having a conventional part 100" and a further part 102 of increased molecular weight or ionic charge compared to the corresponding part 100' of the intermediate molecule. As shown in Step E, the target 15' is then isolated in the manner indicated above, i.e. by means of digestion of the template and preferably membrane separation/filtration leaving the isolated target molecule 15'.

The process of forming a "nick" in a DNA molecule, followed by DNA polymerization, is sometimes referred to as "nick translation" and is described in Sambrook, J., Russell, D. W., *Molecular Cloning: A Laboratory Manual*, the third edition, Cold Spring Harbor laboratory, Cold Spring Harbor, N.Y., 2001 (the disclosure of which is incorporated herein by reference), and further information can be obtained from Kelly, W. S., Chalmers, K and Murray, N. E., *Isolation and characterization of a lambdapolA transducing phage*, Proc. Natl. Acad. Sci., USA, Vol. 74, No. 12, pp 5632-5636 (December 1977) (the disclosure of which is also incorporated herein by reference). Essentially, the intermediate target strand of the annealed construct is nicked or cut by the Dnase 1. The 5'-3' exonuclease activity of DNA polymerase (e.g. *E. coli* polymerase 1), removes intermediate molecule part 100' and the 5'-3' polymerase activity of the same enzyme (DNA polymerase) adds deoxynucleotides to the DNA molecule part 100" at the 3'-end of the cut or nick. The net effect of this cutting, removal and addition of deoxyribonucleotides is a generalized replacement of part 100' by extension of part 100" thus forming molecule part 102. In the presence of specialized deoxynucleotide triphosphates in the medium, these monomers become incorporated into the molecule part 102 being added to the fragment 100" of original intermediate target molecule.

A wide variety of deoxyribonucleases (Dnases) is known, which differ in their substrate specificities, and may be sequence-specific, so that the break may be produced at a precise location within the intermediate target molecule 100; however, this is not essential. However, a Dnase that is specific for single-stranded molecules is employed in this form of the invention. For example, deoxyribonuclease 1 cleaves DNA preferentially at phosphodiester linkages adjacent to a pyrimidine nucleotide, yielding 5'-phosphate terminated polynucleotides with a free hydroxyl group on position 3', on average producing tetranucleotides. It acts on single-stranded DNA.

A wide variety of modified nucleotides that can be incorporated into the target part 102. The modifications to the nucleotides occur within either the nucleotide base, the ribose, or the phosphate to increase molecular weight or ionic charge. Examples include adenosine-5'-(1-thiotriphosphate) and cytidine-5'-(1-thiotriphoshpate). Modified nucleotides with 5-fluorescein (MW 816.7) 6-carboxyfluorescein (MW 537.5) and Texas red (MW 744.1) can be purchased from number of vendors (e.g. Integrated DNA Technologies, IL, USA). Substituting these for regular nucleotides (average MW 330) increases the total molecular weight of the synthesized target. Of course, it may alternatively be possible to incorporate dNTPs of reduced molecular weight compared to natural dNTPs, but this is less preferred.

Similarly, dNTPs of increased ionic charge may be incorporated into the target molecule in the same way. Molecules of different ionic charge act differently during gel separation by means of electrophoresis, and can thus improve methods of separation.

Figure 4:
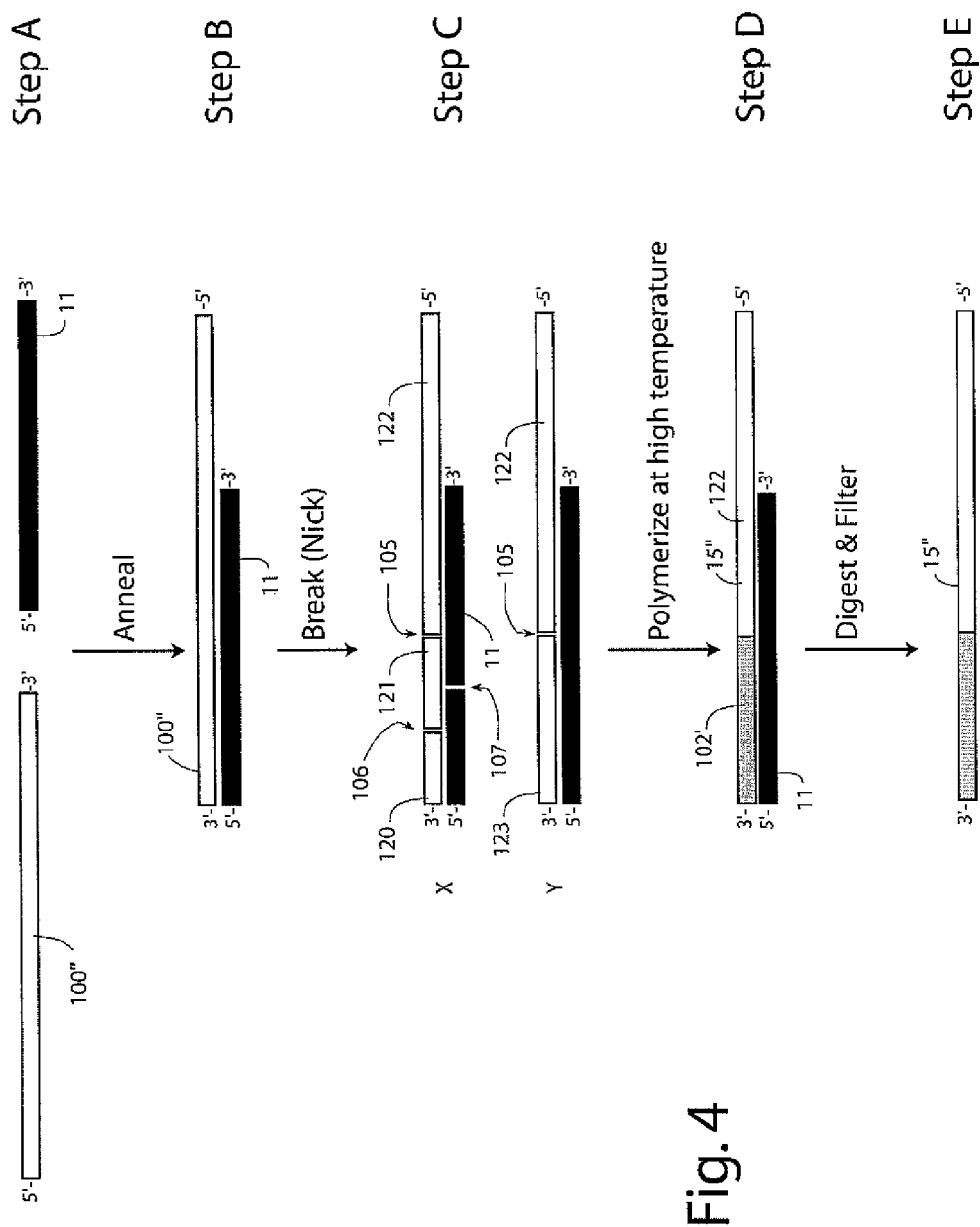
FIG. 4 is another diagram illustrating, in simple form, an alternative embodiment of the invention.

FIG. 4 illustrates a variation of the procedure of FIG. 3 which produces a target molecule 15" that is both long (e.g. having more than 100 bases) and of increased molecular weight or ionic charge. With increased length, there is a greater risk of a cut or nick being formed at more than one location in the molecule.

In Step A, an intermediate molecule 100" is provided that is longer than the template molecule 11, but that has a part that is complementary to template 11. In Step B, these molecules are allowed to anneal. Being longer, part of the intermediate molecule 100" overhangs the template 11 at the 3' end of the template, as shown (the respective sequences are chosen to produce such a mutual alignment).

Step C involves contacting the annealed construct with Dnase 1 used at very low concentration (e.g. 2 μl of DNase 1 solution with DNase 1 at 0.5 U/μl) so that there is minimal cutting of the intermediate molecule, i.e. preferably one or two nicks per intermediate molecule. Normally, there is just one nick formed for every 300-500 bases at low concentration. There may additionally be nicking of the template molecule 11. Therefore, FIG. 4 shows two versions of the nicked construct labeled X and Y, i.e. one (X) having two nicks 105 and 106 in the intermediate molecule 100" forming fragments 120 and 121 with about 30 nucleotides corresponding to the annealing region of the template molecule 11 and a longer fragment 122, together with one nick 107 in the template 11, and another construct (Y) having just one nick 105 in the intermediate molecule 100" forming fragments 122 and 123, and no nicks in the template molecule 11.

Polymerization is then commenced as shown in Step D. This is carried out at a high temperature (e.g. a melting temperature Tm of 80° C.) so that (in the case of construct X) nick fragments with short annealing segments (e.g. 120 and 121) will not continue to bind to the template (i.e. they have low Tm, e.g. less than Tm 50° C.) and polymerize, thus leaving a desired nick fragment 122 bound to the template and polymerized, thus obtaining the extended target 15" containing a section 102' containing nucleotides of higher molecular weight or ionic charge than those in the intermediate molecule 100". In the case of construct Y, the replacement of part 123 with part 102' is the same as for the embodiment of FIG. 3. In both cases, therefore, a target molecule 15" is formed, so the additional nicking does not affect the result.

After the formation of the target 15", the template may be digested as before and the products subjected to filtration to isolate the single-stranded target molecule 15", as shown in Step E.

The invention is illustrated in further detail by reference to the following Examples which are not intended to limit the scope of the present invention.

Example 1

Synthesis of Base Target Oligonucleotide

A 50 mer oligonucleotide is synthesized using solid phase synthesis in a nucleic acid synthesizer (Integrated DNA Technologies, Illinois, USA). For this example, the template sequence is:

3'-
AGTAGATATAGAATAGTCCACTACGATGACGCCATAGCTAGCATGGATAG-
5'

Synthesis of Template Oligonucleotide

A 50 mer oligonucleotide is synthesized using solid phase synthesis using solid phase synthesis in a nucleic acid synthesizer (Integrated DNA Technologies, Illinois, USA). The target sequence is:

5'-
GUACUGCCAAUGGUCUUCAUUCAGGAAACCUCAUCUAUAUCUUAUCAGGU-
3'

Extension of Target Oligonucleotide Using DNA Polymerase
  a. Reactions are carried out in two 1.5 ml Eppendorf tubes as follows:

| | |
|---|---|
| i. Template oligonucleotide (20 μM) | 100 μl |
| ii. Target oligonucleotide (20 μM) | 100 μl |
| iii. Buffer (10X) | 50 μl |
| iv. dNTP (3.12 nM) | 20 μl |
| v. DNA polymerase | 10 units |
| vi. Water (to 500 μl). | | b. Incubated at 37° C. for 1 hour.

Reagents iii, iv, v are from Applied Bisosystems, USA, and reagent vi is from Invitrogen, USA.

Annealing produced the following construct:

```
                    3'-AGTAGATATAGAATAGTCCACTACGATGACGCCATAGCTAGCATGGATAG-5'
5'-GUACUGCCAAUGGUCUUCAUUCAGGAAACCUCAUCUAUAUCUUAUCAGGU-3'
```

After extension, the sequence of the target is as follows:

```
3-GGTTACCAGAAGTAAGTCCTTTCCAGTAGATATAGAATAGTCCACTACGATGACGCCATAGCTAGCATGGATAG-5'
```

Digestion Using N-Uracyl Glucosylase
  c. Add 1 unit of ampErase® (Applied Biosystems, USA)
  d. Incubate at 50° C. for 5 min.

Separation of Extended Template
  e. Use (Princeton separation, NJ. USA).
  f. Add 250 µl volume of PCR binding buffer to 250 µl volume of reaction product, and mix by pipetting 3 times.
  g. Place a single filter column in a 2 ml wash tube and transfer the DNA mixture to the column (filter) and centrifuge at 600 rpm for 1 min.
  h. Add 400 µl wash buffer to the filter column and centrifuge at 6000 rpm for 1 min. Discard the filtrate.
  i. Repeat step (j) once more.
  j. Centrifuge the column at 14000 rpm for 2 min to ensure filter is dry.
  k. Add 50 µl elution buffer and leave for 5 min.
  l. Place the filter column in a sterile 1.5 ml collection tube and centrifuge at 14000 rpm for 2 min. Discard the filter column and save effluent (sample). Store at 4° C. until needed.

Example 2

Synthesis of Base Target Oligonucleotide

A 40 mer oligonucleotide AND A 50 mer oligonucleotide is synthesized using solid phase synthesis in a nucleic acid synthesizer (Integrated DNA Technologies, Illinois, USA). For this example, the template sequence is:

```
3'-GCTAGATGACTATGATCTCTCATGAGTTGTAAGTCCTTTGC-5'           (40mer)
3'AGTAGATATAGAATAGTCCACTACGATGACGCCATAGCTAGCATGGATAG5'    (50mer)
```

Synthesis of Template Oligonucleotide

A 50 mer oligonucleotide is synthesized using solid phase synthesis using solid phase synthesis in a nucleic acid synthesizer (Integrated DNA Technologies, Illinois, USA). The target sequence is:

```
5'-
GUACUGCCAAUGGUCUUCAUUCAGGAAACCUCAUCUAUAUCUUAUCAGGU-
3'
```

Annealing of the two target oligonucleotides to the template

```
3'GCTAGATGACTATGATCTCTCATGAGTTGTAAGTCCTTTGCAGTAGATATAGAATAGTCCACTACGATGACGCCATAGCTAGCATGGATAG5'

5'-GUACUGCCAAUCCUCUUCAUUCAGGAAACCUCAUCUAUAUCUUAUCAGGU-3'
```

Ligation of Target Oligonucleotides Using T4 DNA Ligase

Reactions carried out in set in two 1.5 ml Eppendorf tubes as follows:

| | | |
|---|---|---|
| i. Template oligonucleotide(20 μM) | 100 μl | |
| ii. Target oligonucleotide (20 μM) | 100 μl | |
| iii. Ligase Buffer (10X) | 50 μl | |
| iv. dNTP (3.12 nM) | 20 μl | |
| v. T$_4$ DNA ligase | 10 units | |
| vi. Water (to 500 μl). | | | m. Incubated at 14° C. for 1 hour.

Reagents iii, iv, v, vi are from Invitrogen, USA.

After extension, the sequence of the target is as follows:

3'GCTAGATGACTATGATCTCTCATGAGT-TGTAAGTCCTTTGCAGTAGATATAGAATAGTCCACTACGATGACGCCATAGCTAGCATGGATAG5

Digestion Using N-Uracyl Glucosylase
  n. Add 1 unit of ampErase® (Applied Biosystems, USA)
  o. Incubate at 50° C. for 5 min.

Separation of Extended Template
  p. Use (Princeton separation, NJ. USA).
  q. Add 250 μl volume of PCR binding buffer to 250 μl volume of reaction product, and mix by pipetting 3 times.
  r. Place a single filter column in a 2 ml wash tube and transfer the DNA mixture to the column (filter) and centrifuge at 6000 rpm for 1 min.
  s. Add 400 μl wash buffer to the filter column and centrifuge at 6000 rpm for 1 min. Discard the filtrate.
  t. Repeat step (j) once more.
  u. Centrifuge the column at 14000 rpm for 2 min to ensure filter is dry.
  v. Add 50 μl elution buffer and leave for 5 min.

Place the filter column in a sterile 1.5 ml collection tube and centrifuge at 14000 rpm for 2 min. Discard the filter column and save effluent (sample). Store at 4° C. until needed.

The invention claimed is:

1. A method of producing a single-stranded polynucleotide molecule, which comprises:

providing a template polynucleotide molecule having a sequence of bases complementary to a target polynucleotide molecule, said template sequence including at least one uracil base;

annealing to the template molecule an intermediate polynucleotide molecule having a sequence complementary to the template molecule;

cutting the intermediate polynucleotide molecule into two fragments while annealed to said template molecule and extending one of said fragments to replace the other by nucleotide polymerization employing nucleotide monomers of increased molecular weight or ionic charge compared to nucleotide monomer residues forming said intermediate molecule, thereby forming said target polynucleotide molecule having sequence complementary to said template; and separating said template from said target polynucleotide molecule, thereby forming a single-stranded target polynucleotide molecule.

2. The method of claim 1, wherein said template is separated from said target molecule by digesting said template molecule with a digestion enzyme specific to polynucleotide molecules containing uracil bases.

3. The method of claim 2, wherein said digesting is carried out with uracil-N-glucocylase as said digesting enzyme.

4. The method of claim 1, wherein said cutting of said intermediate polynucleotide molecule is carried out by reacting said intermediate molecule with a deoxyribonuclease enzyme.

5. The method of claim 1, wherein said extending of said one of said fragments is carried out by reacting said one of said fragments while annealed to said template with a DNA polymerase enzyme.

6. The method of claim 1, wherein, following said separation of said target molecule from said template, the target molecule is isolated from remaining reaction products and starting materials.

7. The method of claim 6, wherein said target molecule is isolated from said remaining reaction products and staffing materials by membrane filtration.

* * * * *

```
                        SEQUENCE LISTING

<160> NUMBER OF SEQ ID NOS: 6

<210> SEQ ID NO 1
<211> LENGTH: 50
<212> TYPE: DNA
<213> ORGANISM: Artificial sequence
<220> FEATURE:
<223> OTHER INFORMATION: Chemically synthesized

<400> SEQUENCE: 1
gataggtacg atcgataccg cagtagcatc acctgataag atatagatga            50

<210> SEQ ID NO 2
<211> LENGTH: 50
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (2)..(2)
<223> OTHER INFORMATION: n is uracil
<220> FEATURE:
<221> NAME/KEY: misc_feature
<222> LOCATION: (5)..(5)
<223> OTHER INFORMATION: n is uracil
<220> FEATURE:
<221> NAME/KEY: misc_feature
<222> LOCATION: (11)..(11)
<223> OTHER INFORMATION: n is uracil
<220> FEATURE:
```

```
<221> NAME/KEY: misc_feature
<222> LOCATION: (14)..(14)
<223> OTHER INFORMATION: n is uracil
<220> FEATURE:
<221> NAME/KEY: misc_feature
<222> LOCATION: (16)..(16)
<223> OTHER INFORMATION: n is uracil
<220> FEATURE:
<221> NAME/KEY: misc_feature
<222> LOCATION: (17)..(17)
<223> OTHER INFORMATION: n is uracil
<220> FEATURE:
<221> NAME/KEY: misc_feature
<222> LOCATION: (20)..(20)
<223> OTHER INFORMATION: n is uracil
<220> FEATURE:
<221> NAME/KEY: misc_feature
<222> LOCATION: (21)..(21)
<223> OTHER INFORMATION: n is uracil
<220> FEATURE:
<221> NAME/KEY: misc_feature
<222> LOCATION: (31)..(31)
<223> OTHER INFORMATION: n is uracil
<220> FEATURE:
<221> NAME/KEY: misc_feature
<222> LOCATION: (34)..(34)
<223> OTHER INFORMATION: n is uracil
<220> FEATURE:
<221> NAME/KEY: misc_feature
<222> LOCATION: (36)..(36)
<223> OTHER INFORMATION: n is uracil
<220> FEATURE:
<221> NAME/KEY: misc_feature
<222> LOCATION: (38)..(38)
<223> OTHER INFORMATION: n is uracil
<220> FEATURE:
<221> NAME/KEY: misc_feature
<222> LOCATION: (40)..(40)
<223> OTHER INFORMATION: n is uracil
<220> FEATURE:
<221> NAME/KEY: misc_feature
<222> LOCATION: (42)..(42)
<223> OTHER INFORMATION: n is uracil
<220> FEATURE:
<221> NAME/KEY: misc_feature
<222> LOCATION: (43)..(43)
<223> OTHER INFORMATION: n is uracil
<220> FEATURE:
<221> NAME/KEY: misc_feature
<222> LOCATION: (45)..(45)
<223> OTHER INFORMATION: n is uracil
<220> FEATURE:
<221> NAME/KEY: misc_feature
<222> LOCATION: (50)..(50)
<223> OTHER INFORMATION: n is uracil

<400> SEQUENCE: 2
gnacngccaa nggncnncan ncaggaaacc ncancnanan cnnancaggn            50

<210> SEQ ID NO 3
<211> LENGTH: 74
<212> TYPE: DNA
<213> ORGANISM: Artificial sequence
<220> FEATURE:
<223> OTHER INFORMATION: Chemically synthesized

<400> SEQUENCE: 3
gataggtacg atcgataccg cagtagcatc acctgataag atatagatga cctttcctga   60
atgaagacca ttgg                                                    74

<210> SEQ ID NO 4
<211> LENGTH: 41
<212> TYPE: DNA
<213> ORGANISM: Artificial sequence
```

-continued

```
<220> FEATURE:
<223> OTHER INFORMATION: Chemically synthesized

<400> SEQUENCE: 4
cgtttcctga atgttgagta ctctctagta tcagtagatc g                    41

<210> SEQ ID NO 5
<211> LENGTH: 50
<212> TYPE: DNA
<213> ORGANISM: Artificial sequence
<220> FEATURE:
<223> OTHER INFORMATION: Chemically synthesized

<400> SEQUENCE: 5
gataggtacg atcgataccg cagtagcatc acctgataag atatagatga           50

<210> SEQ ID NO 6
<211> LENGTH: 91
<212> TYPE: DNA
<213> ORGANISM: Artificial sequence
<220> FEATURE:
<223> OTHER INFORMATION: Chemically synthesized

<400> SEQUENCE: 6
gataggtacg atcgataccg cagtagcatc acctgataag atatagatga cgtttcctga    60
atgttgagta ctctctagta tcagtagatc g                                   91
```